Figure 1:
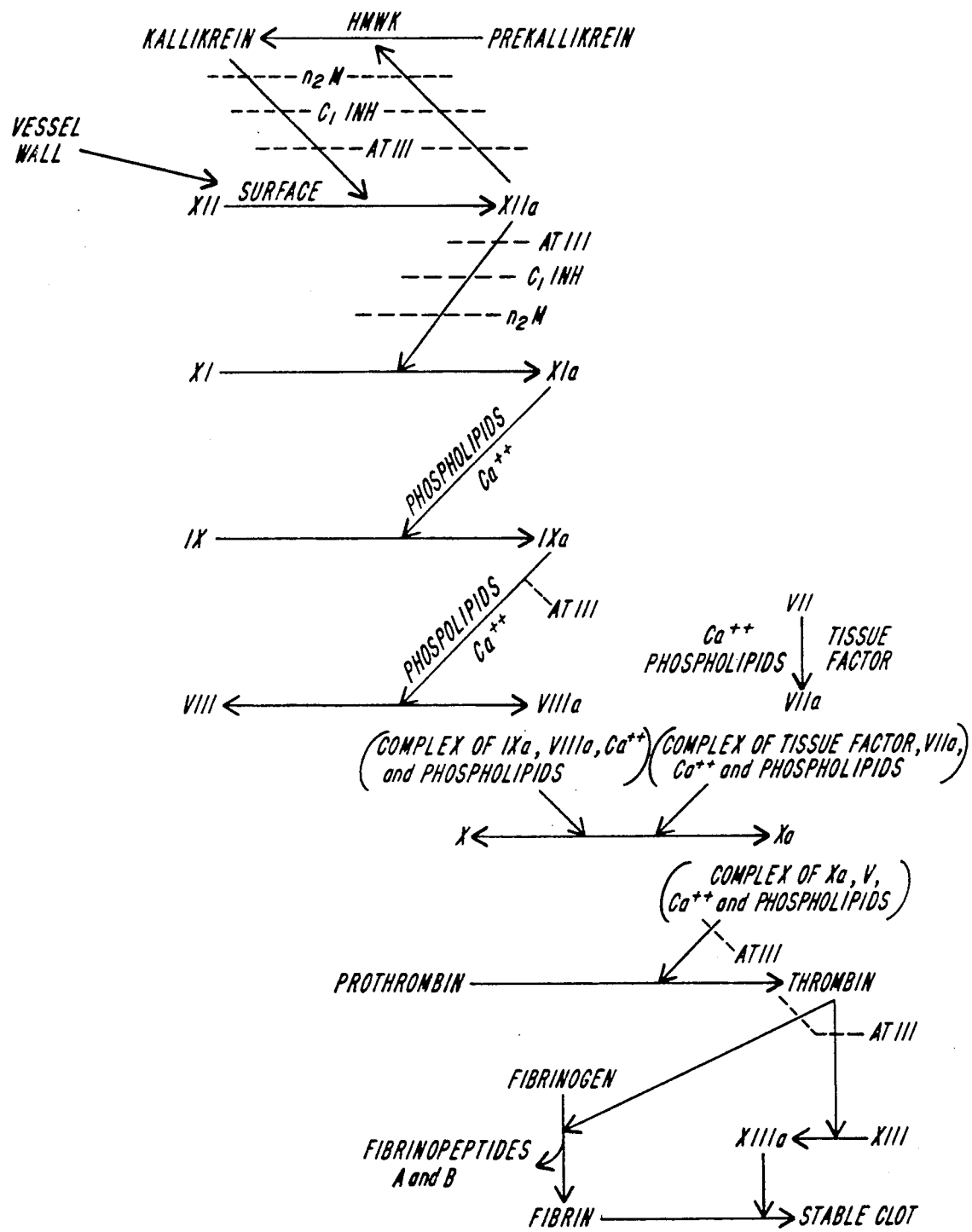

United States Patent [19]

Ito et al.

[11] Patent Number: 5,126,140

[45] Date of Patent: * Jun. 30, 1992

[54] THROMBOMODULIN-COATED BICOMPATIBLE SUBSTANCE

[75] Inventors: Ralph K. Ito, Quincy; Frank W. LoGerfo, Belmont, both of Mass.

[73] Assignee: New England Deaconess Hospital Corporation, Boston, Mass.

[*] Notice: The portion of the term of this patent subsequent to May 28, 2008 has been disclaimed.

[21] Appl. No.: 382,411

[22] Filed: Jul. 24, 1989

Related U.S. Application Data

[63] Continuation-in-part of Ser. No. 227,728, Aug. 3, 1988.

[51] Int. Cl.[5] .............................. A61F 2/00; A61K 9/22
[52] U.S. Cl. ..................................... 424/423; 424/422; 424/424; 424/425; 424/426; 523/112; 523/113; 530/395; 604/890.1
[58] Field of Search .................. 424/422, 423-426; 530/395; 523/112, 113

[56] References Cited

U.S. PATENT DOCUMENTS

| | | | |
|---|---|---|---|
| 4,116,898 | 9/1978 | Dudley et al. | 523/112 |
| 4,600,652 | 7/1986 | Solomon et al. | 428/423.3 |
| 4,720,512 | 1/1988 | Hu et al. | 523/112 |

Primary Examiner—Thurman Page
Assistant Examiner—G. S. Kishore
Attorney, Agent, or Firm—Lahive & Cockfield

[57] ABSTRACT

Disclosed is a biocompatible, thromboresistant substance useful for implantable and extracorporeal devices in contact with the vascular system, and methods for producing the same. The biocompatible, thromboresistant substance comprises a synthetic, biocompatible material, at least one biocompatible base coat layer adhered to at least one surface of the material, and the thrombogenesis inhibitor thrombomodulin immobilized on the base coat layer via a component capable of binding the inhibitor without affecting its thrombogenesis-inhibiting activity.

31 Claims, 6 Drawing Sheets (FROM ESMON (1989) PROG. HEMOST. THROMB. 9:29-55)

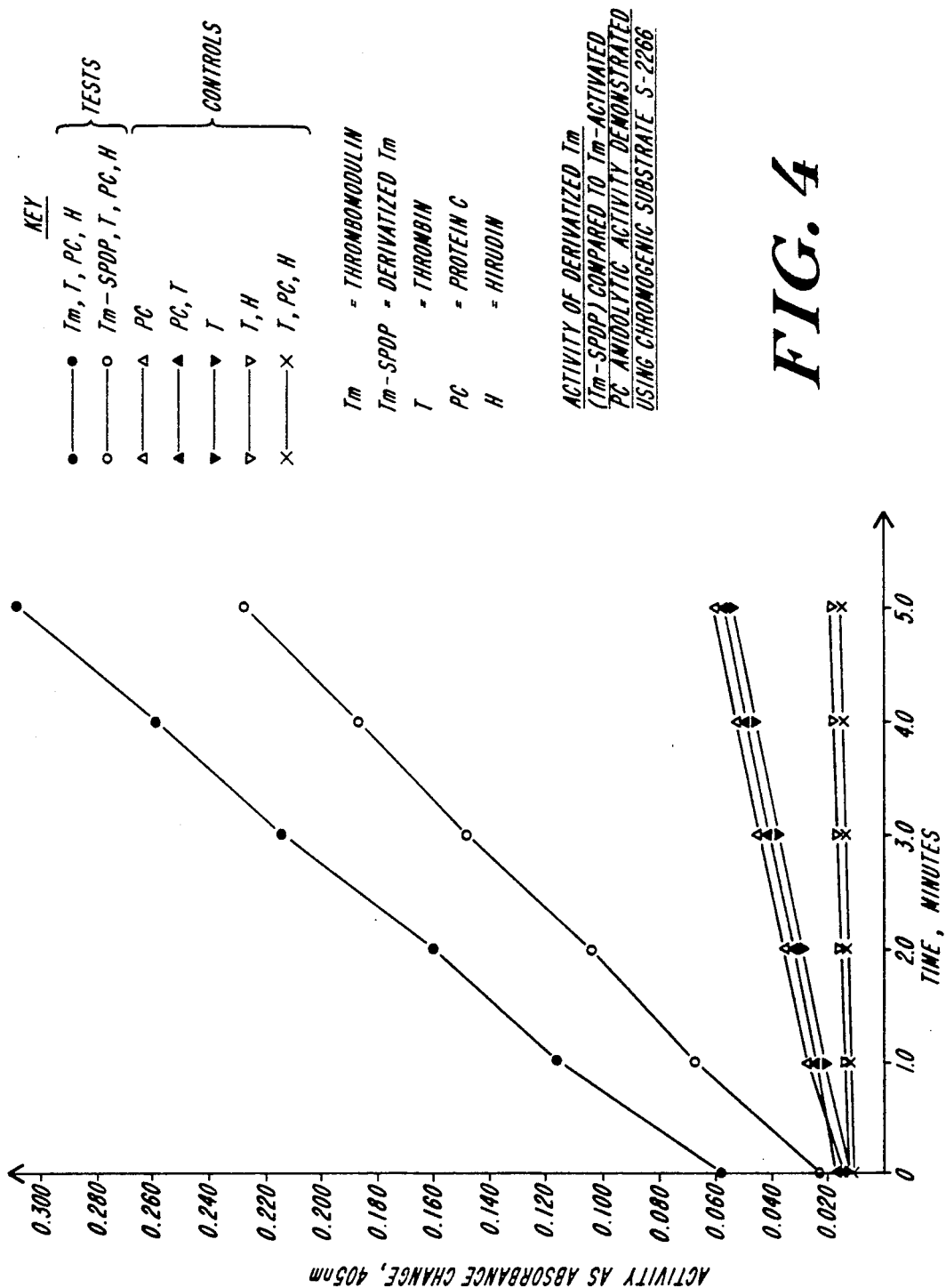

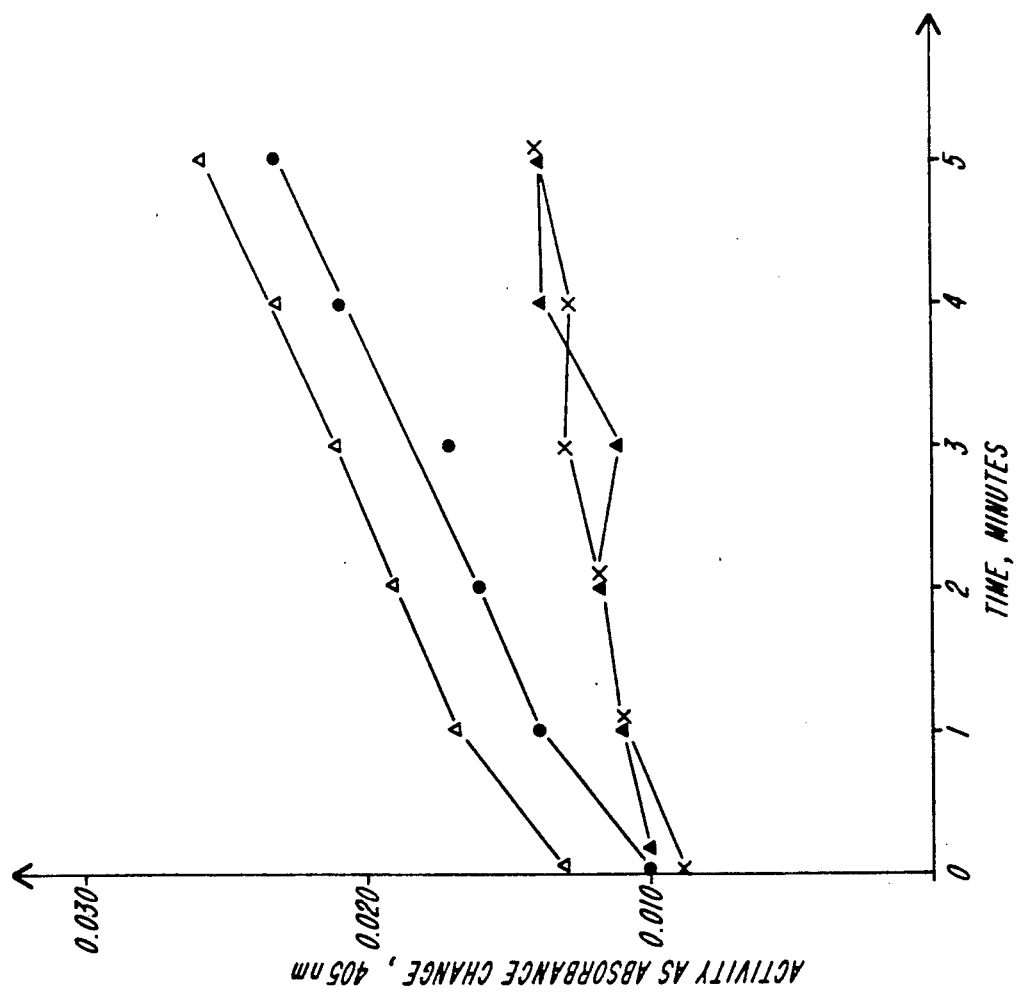

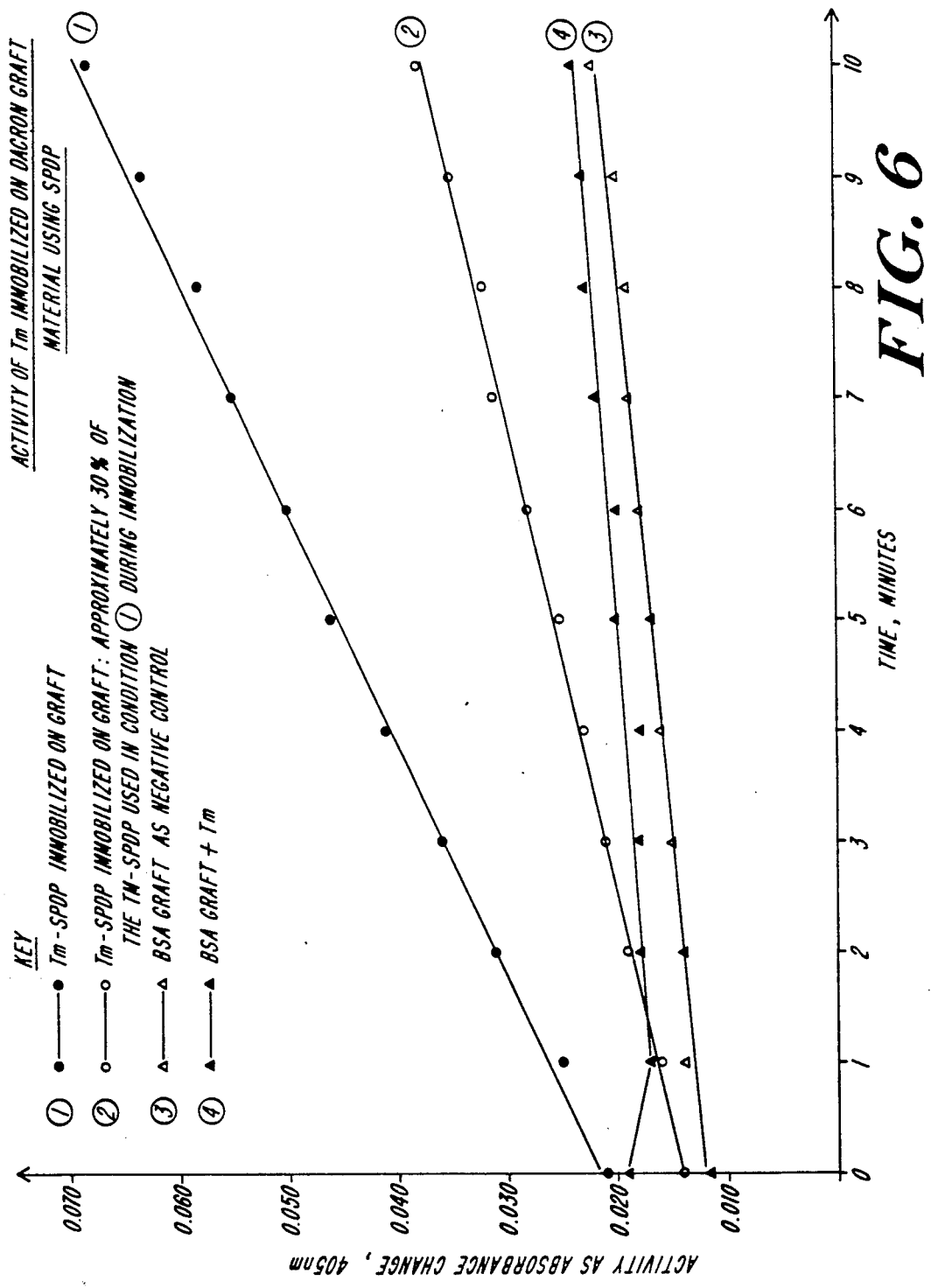

THROMBOMODULIN-COATED BICOMPATIBLE SUBSTANCE

CROSS-REFERENCE TO RELATED APPLICATION

This application is a continuation-in-part of applicants' copending application Ser. No. 227,728, entitled "BIOCOMPATIBLE SUBSTANCE WITH THROMBORESISTANCE" (NEL-183A), filed Aug. 3, 1988.

BACKGROUND OF THE INVENTION

The technical field of the present invention is prosthetic vascular materials, and more specifically is biocompatible, thromboresistant vascular substances and methods of their preparation.

Exposure of blood to artificial surfaces usually leads to deposition of a layer of adherent platelets, accompanied by activation of the intrinsic coagulation system, and ultimately to the formation of a thrombus. In fact, significant blood/materials interaction can occur on a single pass through a prosthetic arterial graft. The types of blood proteins initially adsorbed or bound to synthetic surfaces may include proteins involved in contact coagulation. Contact coagulation or the extrinsic pathway of coagulation is a complex pathway of biochemical events that induces fibrin formation, platelet and complement activation, chemotaxis, kinin generation, and activation of fibrinolytic components. In addition, each of these events augments subsequent biochemical pathways often controlled by positive and negative feedback loops. Thus, thrombosis induced by contact with artificial materials is a major obstacle in the development and use of internal prostheses and extracorporeal devices such as artificial vessels and organs, and cardiopulmonary bypass and hemodialysis equipment.

Materials having varying degrees of thromboresistance have been utilized in vascular prostheses with limited success. These materials include corroding (self-cleaning) metals, synthetic polymers such as polydimethyl siloxane, Teflon, acylates and methacrylates such as Dacron, electrets, anionic copolymers, and hydrogels (for a review see Salzman et al. (1987) in *Hemostasis and Thrombosis, Basic Principles and Clinical Practice* (Colman et al., eds.) J. B. Lippincott Co., Phila., Pa., pp. 1335-1347).

To decrease the chances of thrombosis due to extended periods of contact with such artificial materials, patients have been treated with systemically administered anti-coagulant, anti-platelet, and thrombolytic drugs. These include any compound which selectively inhibits thromboxane synthetase without affecting prostacycline synthetase, affects platelet adherence as well as aggregation and release, enhances vascular PGI2 production, and/or inhibits both thrombin- and thromboxane-mediated platelet aggregation. Such compounds include aspirin, sulfinpyrazone, dipyridamole, ticlopidine, and suloctidil. However, treatment with these drugs often elicits unwanted side effects including systemic hemmorhaging and the inability to initiate and complete desired clotting elsewhere in the body.

To improve on the thromboresistance of artificial materials, biologically active molecules having thrombolytic, anticoagulating, thrombogenesis-inhibiting, and/or platelet inhibiting abilities have been linked thereto. For example, heparin has been bound to artificial surfaces to reduce coagulation by activating variuous inhibitors of the intrinsic clotting system (Salzman et al. (1987) in *Hemostasis and Thrombosis: Basic Principles and Clinical Practice*, 2nd Ed., (Colman et al., eds.), Lippincott Co., Phila., Pa., pp 1335-1347). However, heparin enhances platelet responses to stimuli such as ADP or collagen, and promotes two adverse primary blood responses towards synthetic surfaces: platelet adhesion and aggregation. In addition, although surface-bound heparin/antithrombin complex may be passive towards platelets, the wide variety of effects it has on interactions with endothelial cell growth factor, inhibition of smooth muscle proliferation, and activation of lipoprotein lipase raises questions as to what adverse effects it may induce over time.

Anti-platelet agents such as $PGE_1$, $PGI_2$ (experimental use only), cyclic AMP, and aspirin have also been attached to solid polymer surfaces. These agents discourage the release of platelet factors that stimulate adverse healing responses in the vicinity of a vascular graft. They may also reduce platelet-aided thrombus formation by inhibiting platelet adhesion.

The exposure of many artificial surfaces to albumin prior to vascular contact results in reduced reactivity with platelets (NIH Publication No. 85-2185, September, 1985, pp. 19-63). Therefore, albumin has been used to coat extracorporeal surfaces before cardiopulmonary by-pass surgery. However, long-term thromboresistance has not been achieved by this procedure.

Fibrinolytically active streptokinase and urokinase, alone or in combination with heparin have been attached to artificial surfaces by Kusserow et al (Trans. Am. Soc. Artif. Intern. Organs (1971) 17:1). These enzymes reduce excessive fibrin deposition and/or thrombotic occlusions. However, the long term assessment of their ability to confer thromboresistance to a synthetic surface has not been determined.

Surface active agents such as Pluronic F-68 have also been immobilized on artificial surfaces, but do not appear to offer long term blood compatibility (Salyer et al. (1971) *Medical Applications of Plastics*, Biomed. Materials Res. Sym. (Gregor, ed.) No. 1 pp. 105).

Therefore, what is needed are better biocompatible materials which are thromboresistant in the long term and whose active components do not cause detrimental side affects.

An object of the present invention is to provide a synthetic, biocompatible, thromboresistent material useful for implantable and extracorporeal devices in contact with bodily fluids Another object is to provide an immobilized thrombogenesis inhibitor which is biologically active, and a method of preparing the same.

Still another object of this invention is to provide a method of inhibiting platelet aggregation, the release of platelet factors, and thrombogenesis at the localized site of the graft or prosthesis-blood interface, thus avoiding the systemic effect of antiplatelet and antithrombosis drugs.

SUMMARY OF THE INVENTION

Materials and methods are disclosed herein for the provision of biocompatible, thromboresistant substances useful as a component of implantable or extracorporeal devices in contact with the blood.

Figure 2:
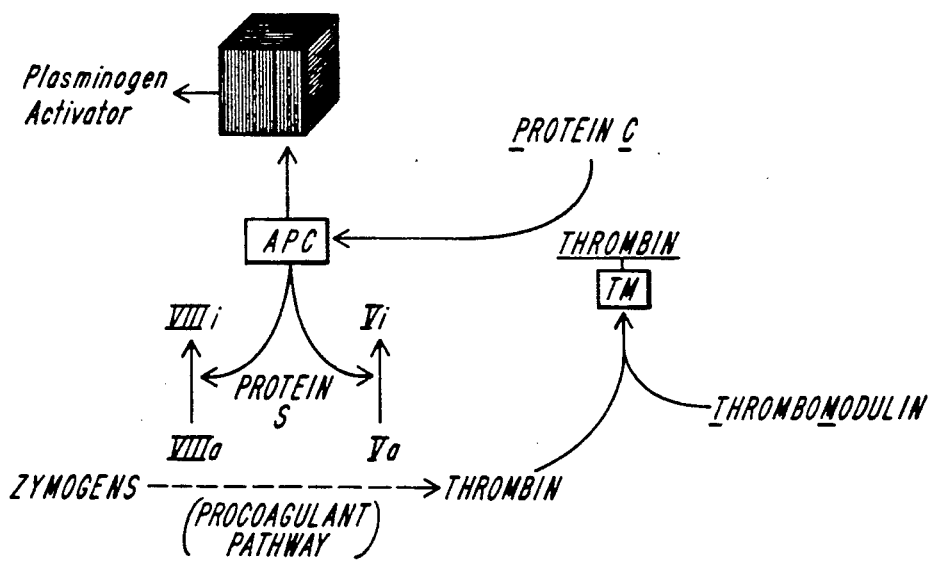

It has been discovered that a synthetic, biocompatible material can be made into a thromboresistant substance by immobilizing to it, by way of a base coat layer, the thrombogenesis inhibitor thrombomodulin, or active analogs or active fragments thereof, in such a way that does not compromise the thrombogenesis inhibiting activity of thrombomodulin.

The term "thrombogenesis inhibitor" is used herein to describe a native, synthetic, or recombinant protein, or fragment thereof having the physical and biochemical characteristics of thrombomodulin. Thrombomodulin modulates the coagulation pathway by behaving as a cofactor in the activation of Protein C by thrombin. Activated Protein C in the presence of Protein S degrades active Factors V and VIII, cofactors which are necessary for coagulation, thereby turning off the coagulation pathway.

Synthetic materials contemplated by the instant invention are preferably polymers such as polyethylene terephthalate (i.e., Dacron or Amilar), nylon, polyurethane, cross-linked collagen, polytetrafluoroethylene, polyglycolic acid, and mixtures thereof, the most preferred polymeric material being woven polyethylene terephthalate. Other synthetic materials may also be used.

In accordance with the invention, the thrombogenesis inhibitor is immobilized on the synthetic material via a base coat layer which is adhered to least one surface of the synthetic material. The base coat contains a component capable of binding the thrombogenesis inhibitor without compromising the biological activity of the inhibitor. Examples of such thrombogenesis inhibitor-binding base coat components include proteins, peptides, lipoproteins, glycoproteins, glycosaminoglycans, hydrogels, synthetic polymers, and mixtures thereof. In preferred aspects of the invention, the base coat layer includes a protein component such as serum albumin, fibronectin, or mixtures of these proteins, and in particular, human serum albumin or human fibronectin.

In preferred aspects of the invention, the synthetic material is activated prior to having the base coat layer adhered thereto to enhance its ability to bind the base coat base layer. In one exemplary aspect, the synthetic material is contacted with a solution which makes available at least one chemically active group (e.g., a carboxylic acid group) in the material for binding to a bifunctional cross-linking reagent (e.g., carbodiimide). The material so treated is then put into contact with a solution containing the cross-linking reagent for a time sufficient to allow the chemically active group to bind to the reagent. Prior to the activation step, the synthetic material may be contacted with a solution which removes impuritities therein and/or thereon prior to the activation step described above.

The immobilization step may be carried out by initially contacting the thrombogenesis inhibitor with at least one molecule of a bifunctional cross-linking reagent for a time sufficient to allow linking of the reagent to the inhibitor, and then binding the thrombogenesis inhibitor-linked reagent to the base coat layer adhered to the synthetic material. The thrombogenesis inhibitor retains its thrombogenesis inhibiting activity when bound to the reagent.

The term "bifunctional cross-linking reagent" is defined herein as a molecule having the ability to bind to, and therefore link, two reactive groups on, for example, one molecule or two separate molecules. If the bifunctional cross-linking reagent binds two different types of groups, it is a "heterobifunctional" cross-linking reagent. However, if the bifunctional cross-linking reagent binds only to two similar groups, it is "homobifunctional". Useful bifunctional cross-linking reagents include any number of known heterobifunctional or homobifunctional reagents, or a mixture of both.

Prior to the binding step, the thrombogenesis inhibitor-bound cross-linking reagent may be subjected to chromatographic procedures to remove impurities mixed in with it.

In one aspect of the invention, the base coat adhered to the synthetic material may be linked to at least one molecule of a bifunctional cross-linking reagent. In this embodiment, the method further includes binding the thrombogenesis inhibitor-bound reagent to the base coat-linked reagent, thereby linking the thrombogenesis inhibitor to the synthetic material-adhered base coat layer.

In another aspect of the invention, the base coat-linked reagent is reduced prior to the binding step. Reduction results in the formation of sulfhydryl groups on the base coat-linked reagent which can react with the inhibitor-linked bifunctional reagent via a substitution reaction to form a disulfide bond, thereby covalently linking the thrombogenesis inhibitor to the base coat layer.

In an alternative embodiment of the invention, the thrombogenesis inhibitor is linked to base coat material prior to its immobilization on the synthetic material.

The invention will next be described in connection with certain illustrated embodiments. However, it should be clear that various modifications, additions, and deletions can be made without departing from the spirit or scope of the invention.

BRIEF DESCRIPTION OF THE DRAWING

The foregoing and other objects of the present invention, the various features thereof, as well as the inventions thereof may be more fully understood from the following description when read together with the accompanying drawings in which:

FIG. 1 is a diagrammatic representation of the pathways involved in coagulation;

FIG. 2 is a diagrammatic representation of pathways involved in protein C activation and expression;

FIG. 3 is a schematic representation of the amino acid sequence of native thrombomodulin;

FIG. 4 is a graphic representation of the activity of TM derivatized with SPDP;

FIG. 5 is a graphic representation of the activities of grafts including immobilized TM or BSA; and FIG. 6 is a graphic representation of the activities of TM- or BSA-immobilized grafts.

DESCRIPTION OF THE INVENTION

This invention provides biocompatible, thromboresistant substances useful for implantable and extracorporeal devices in contact with the vascular system, and methods for their fabrication.

The substances provided by this invention include a biocompatible synthetic substance having the thrombogenesis inhibitor, thrombomodulin, linked thereto via a biocompatible base coat adhered to the surface of the synthetic material.

Thrombomodulin is a receptor protein found surface of endothelial and other cells which is involved in the regulation of coagulation, the various pathways of which are shown in FIG. 1. Thrombomodulin is a glycoprotein of about 60.3 kD molecular weight and approximately 575 amino acids (Esmon (1989) Prog. Hemost. Thromb. 9:29-55). Thrombomodulin binds thrombin, and in doing so, acts as a cofactor in the activation of Protein C by thrombin; it accelerates the binding of thrombin to the inactive form of Protein C (FIG. 2), thereby forming activated Protein C. Activated Protein C exhibits both anticoagulant and thrombolytic activities: it inhibits the clotting cascade at the levels of Factors V and VIII by the enzymatic cleavage of the activated forms of these clotting factors, and it takes part in the production of plasminogen activator, a protein with thrombolytic activity. Throbomodulin also inhibits blood coagulation by inhibiting the unbound thrombin-catalyzed cleavage of inactive fibrinogen to fibrin (see e.g., Esmon et al. (1982) J. Biol. Chem. 257:7944-7947), and by the inhibiting platelet aggregation by blocking the ability of thrombin to activate platelets (see e.g., Murata et al. (1988) Thrombosis Res. 50:647-656 and Esmon et al. (1983) J. Biol. Chem. 20:12238-12242).

The material useful in a prosthetic extracorporeal or implantable device may be composed of any biocompatible, synthetic, preferably polymeric material having enough tensile strength to withstand the rigors of blood circulation, and having groups onto which a base coat can be directly or indirectly bound. Examples of such synthetic materials are polytetrafluoroethylene (Teflon), polyethylene terephthalate (Dacron or Amilar), nylon, and the like. The material may have any dimensions suitable for the purpose for which it is being used. For example, it may be an integral part of an implanted heart valve or of an extracorporeal device used for hemodialysis or cardiopulmonary by-pass surgery, or it may be used to coat catheters or to line the interior of a vascular graft.

The synthetic material, when obtained, may be coated with or contain various noncovalently adhered impurities whose removal may be prerequisite for the adherence of a base coat thereto. For example, lubricants on commercial quality woven polyethylene terephthalate can be removed by contacting the polyethylene terephthalate with a solution containing, for example, various detergents, solvents, or salts, which loosen and/or solubilize these impurities.

TABLES 1 and 2 outline representative methods of preparing the biocompatible, thromboresistant substance, where "Da" refers to a synthetic material composed of woven polyethylene terephthalate fibers, "HSA" refers to human serum albumin, "EDC" refers to carbodiimide, "SPDP" refers to N-succinimidyl 3-(2-pyridyldithio)-propionate, "P-2-T" refers to pyridine-2-thione, and "Inhibitor" refers to thrombomodulin or an active fragment or active analog thereof.

TABLE 1

| STEP | PROCESS |
| --- | --- |
| (1) | Da + NaOH → Da-COOH |
| (2) | Da-COOH + EDC → Da-EDC |
| (3) | Da-EDC + HSA → Da-HSA + urea |
| (4) | Da-HSA + SPDP → Da-HSA-SPDP |
| (5) | Da-HSA-SPDP + DTT → Da-HSA-SH + P-2-T |
| (6) | Inhibitor + SPDP → Inhibitor-SPDP |
| (7) | Da-HSA-SH + Inhibitor-SPDP → Da-HSA-S—S-Inhibitor + P-2-T |

TABLE 2

| STEP | PROCESS |
| --- | --- |
| (1) | HSA + SPDP → HSA-SPDP |
| (2) | HSA-SPDP + DTT → HSA-SH + P-2-T |
| (3) | Inhibitor + SPDP → Inhibitor-SPDP |

TABLE 2-continued

| STEP | PROCESS |
| --- | --- |
| (4) | HSA-SH + Inhibitor-SPDP → HSA-S-S-Inhibitor + P-2-T |
| (5) | Da + NaOH → Da-COOH |
| (6) | Da-COOH + EDC → Da-EDC |
| (7) | Da-EDC + HSA-S-S-Inhibitor → Da-HSA-S—S-Inhibitor + urea |

Initially, the synthetic material may be activated so as to enhance the binding of the base coat. This activating step increases the number of chemically active groups in the synthetic material. For example, alkaline hydrolysis may be performed to increase the number of reactive carboxylic acid groups in the polyethylene terephthalate to which a bifunctional cross-linking reagent such as carbodiimide may be bound. Ultimately, the base coat will adhere to the bound carbodiimide groups on the synthetic material. However, this method must be performed with care, as alkaline hydrolysis partially degrades the polyethylene terephthalate, resulting in a fraying of the material's fibers. At least one base coat layer is adhered to at least one surface of the synthetic material.

The base coat material, either adhered to the material as a layer or unbound, provides components for attachment thereto of the thrombogenesis inhibitor. Such components provide more binding sites for the inhibitor than does the synthetic material alone, thereby amplifying the amount of inhibitor which may be bound. Useful components include proteins, peptides, lipoproteins, glycoproteins, glycosaminoglycans, synthetic polymers, and mixtures thereof. Proteins such as serum albumin and fibronectin are particularly desirable as base coat components as they are known to have anti-thrombogenic properties, themselves. (Lyman et al. (1965) Trans. Am. Soc. Artif. Intern. Organs 11:301; Falb et al. (1971) Fed. Proc. 30:1688). For example, a molecule of human serum albumin (HSA) has 65 amino groups available as inhibitor-binding sites.

Attachment of the base coat to the surface of the artificial material may be covalent in nature. Methods to covalently bind proteins to polyethylene terephthalate involve attack of the free reactive succinimide ester group of the cross-linking reagent to primary amino groups on a protein. As shown in the example in TABLE 1, to covalently adhere the base coat to polyethylene terephthalate, the polyethylene terephthalate is initially treated with 0.5N NaOH and reacted with carbodiimide under slight acidic conditions before it is coated with HSA (base coat) in phosphate buffered saline (PBS).

The thrombogenesis inhibitor is then covalently adhered to the base coat via the component, producing an inhibitor-coated substance. Inhibitor-coated substances are ideal for use in implantable devices which are in direct contact with blood. For example, by-pass grafts used to replace blood vessels often become filled with blood clots or thrombi, resulting in restricted blood flow. Since the inhibitor-coated substance is resistant to formation of blood clots, its use will prevent thrombosis and subsequent blockage of the bypass graft. Likewise when catheters are placed into the vascular system for a diagnostic or therapeutic purposes, a blood clot often forms on the outside of the catheter. The clot may be washed off the catheter by flowing blood, or be jarred loose by manipulation of the catheter, increasing the possibility of embolism and blockage of the circulation to vital organs. Inhibitor-coated substances provide similar advantages for artificial or prosthetic heart valves, intraaortic balloon pumps, total or artificial heart or heart-assist devices, intracaval devices, and any device in contact with the bloodstream. In addition, inhibitor-coated devices provide advantages for intracavity devices such as intraperitoneal dialysis catheters and subcutaneous implants where the thrombogenesis-induced inflammmatory reactions would be diminished.

Figure 3:
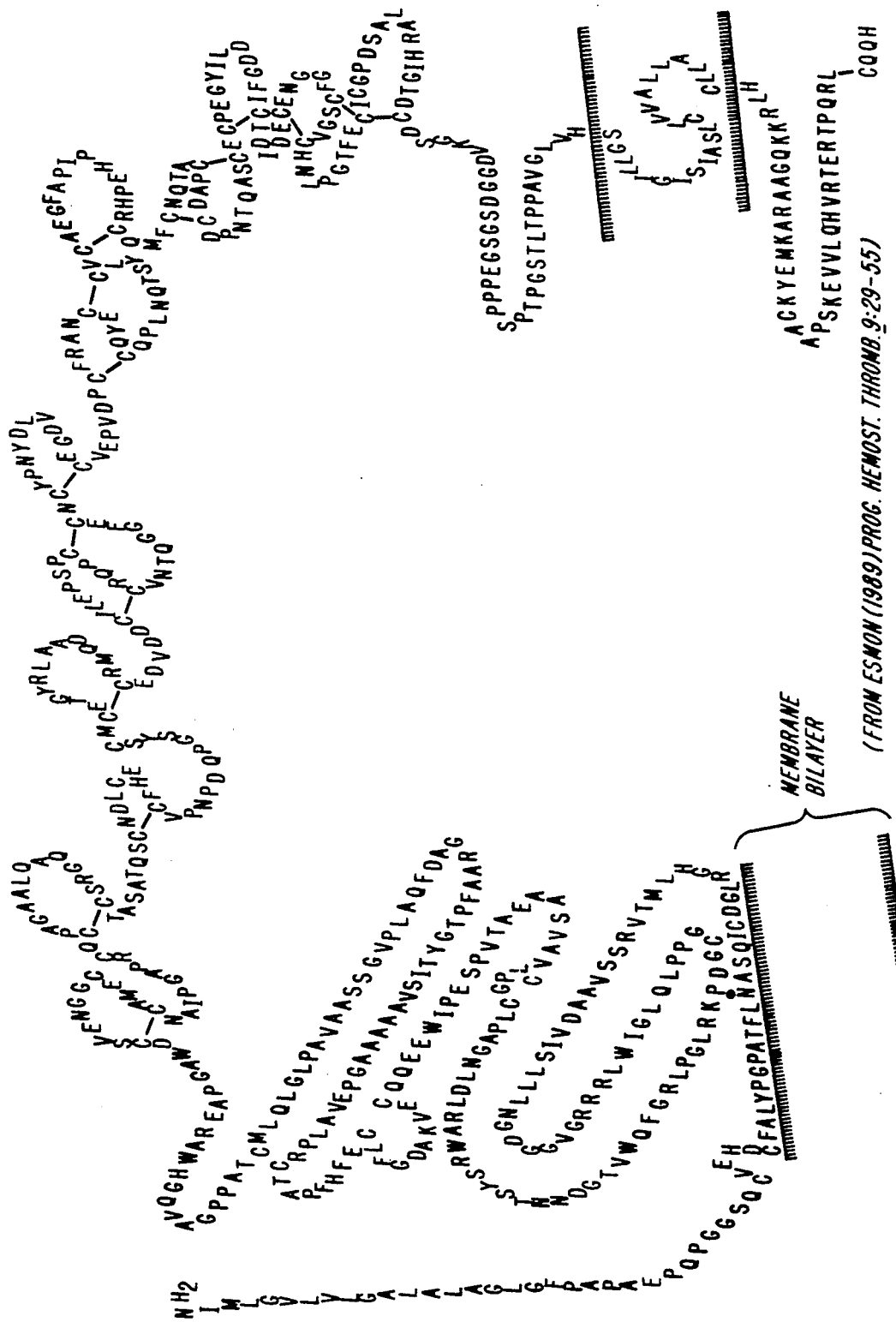

Thrombogenesis inhibitors useful for these purposes include thrombomodulin and active analogs, active fragments, active derivatives, and active fusion products thereof, and mixtures thereof Native thrombomodulin can be obtained in active form from human lung and placenta, the isolation procedures of which are known to those skilled in the art (see e.g., EP 0239644; and Salem et al. (1984) J. Biol. Chem. 259:12246–12251). Thrombomodulin may also be obtained from cultured endothelial cells such as cultured human umbilical vein endothelial cells (Murata et al. (1988) Thrombosis Res. 50:647–656). Alternatively, since its amino acid sequence is known (FIG. 3), synthetic and recombinant forms of thrombomodulin may be produced by known procedures (see e.g., WO 88/09811 and EP 0290419).

The thrombogenesis inhibitor is directly or indirectly immobilized on the base coat via the use of a bifunctional cross-linking reagent. In particular, a heterobifunctional cross-linking reagent which has two different reactive groups at each end of a linear molecule, and can therefore bind two different reactive groups on other molecules or on a different region of the same molecule, is most preferable as the bifunctional cross-linking agent. Useful heterobifunctional reagents include SPDP and succinimidyl 4-(N-maleimidomethyl) cyclohexane-1-carboxylate (SMCC), among many. In addition, photoreactive cross-linkers such as sulfosuccinimidyl 2-(m-azodo-o-nitro-benzamido)-ethyl-1,3'-dithiopropionate (SAND), and N-succinimidyl-6-(4-azoido-2'-nitrophenyl-amino) hexanoate (SANPAH) have a photoreactive group that can directly insert into C—H bonds of the base coat by photochemical coupling, while the other group remains free to bind to proteins. Useful cross-linking reagents and their characteristics are listed in TABLE 3. The "Double-Agent Number" listed for each reagent is the commercial designation for the reagent as made available by Pierce Chemical Co. (Rockford, Ill.).

TABLE 3

| | CROSS-LINKING REAGENTS | | | | |
|---|---|---|---|---|---|
| Double-Agent Number | Double-Agent Acronym | Bifunctionality | | Reactive towards: | |
| | | Homo | Hetero | NH$_2$ | SH | Photo-Reactive |
| 21551 | ANB-NOS | | X | X | | X |
| 20106 | APB | | X | | X | X |
| 20107 | APG | | X | | | X |
| 21559 | APTP | | X | X | X | X |
| 21579 | BS$^3$ | X | | X | | |
| 22319 | BMH | X | | | X | |
| 21554 | BSOCOES | X | | X | | |
| 21524 | DFDNB | X | | X | | |
| 20047 | DIDS | X | | X | | |
| 20664 | DMA | X | | X | | |
| 20666 | DMP | X | | X | | |
| 20668 | DMS | X | | X | | |
| 22585 | DSP | X | | X | | |
| 21555 | DSS | X | | X | | |
| 20590 | DST | X | | X | | |

TABLE 3-continued

| | CROSS-LINKING REAGENTS | | | | |
|---|---|---|---|---|---|
| Double-Agent Number | Double-Agent Acronym | Bifunctionality | | Reactive towards: | |
| | | Homo | Hetero | NH$_2$ | SH | Photo-Reactive |
| 20665 | DTBP | X | | X | | |
| 22590 | DTBPA | X | | | | X |
| 21577 | DTSSP | X | | X | | |
| 21550 | EADB | | X | X | | X |
| 21565 | EGS | X | | X | | |
| 23700 | FNPA | | X | X | | X |
| 21560 | HSAB | | X | X | | X |
| 26095 | MABI | | X | X | | X |
| 22310 | MBS | | X | X | X | |
| 27715 | NHS-ASA | | X | X | | X |
| 20669 | PNP-DTP | | X | X | | X |
| 21552 | SADP | | X | X | | X |
| 21549 | SAND | | X | X | | X |
| 22588 | SANPAH | | X | X | | X |
| 27716 | SASD | | X | X | | X |
| 22325 | SIAB | | X | X | X | X |
| 22320 | SMCC | | X | X | X | |
| 22315 | SMPB | | X | X | X | |
| 21557 | SPDP | | X | X | X | |
| 21556 | Sulfo-BSOCOES | X | | X | | |
| 20591 | Sulfo-DST | X | | X | | |
| 21556 | Sulfo-EGS | X | | X | | |
| 22312 | Sulfo-MBS | | X | X | X | |
| 21553 | Sulfo-SADP | | X | X | | X |
| 22589 | Sulfo-SANPAH | | X | X | | X |
| 22327 | Sulfo-SIAB | | X | X | X | |
| 22322 | Sulfo-SMCC | | X | X | X | |
| 22317 | Sulfo-SMPB | | X | X | X | |
| 26101 | TRAUNT'S | X | | X | | |

The cross-linking reagent is applied to the base coat in amounts such that the desired binding site density is achieved. Binding site density is that amount of cross-linking reagent, in terms of moles/g synthetic material, to bind to the base coat while providing confluent coverage of the surface.

To put the inhibitor in condition for linkage to the base coat, the cross-linkage reagent may be initially coupled to the base coat and to the inhibitor. The kinetic constants of the inhibitors are compared before and after coupling to evaluate effects of the procedure on their kinetic constants. The inhibitor should remain biologically active after being coupled. Therefore, standard activity assays specific for the inhibitor to be immobilized are performed using a standard thrombin solution to evaluate this capacity.

As an alternative, the protein component of the base coat may be bound to the thrombogenesis inhibitor forming a conjugate prior to its adherence to the synthetic material, and the conjugate bound to the synthetic material as shown in TABLE 2. The unbound thrombogenesis inhibitor conjugate retains biological activity, and therefore can be used as an agent with increased half-life in the circulation as it is not easily cleared by the kidney. In addition, derivatization of the thrombogenesis inhibitor with the protein component of the base coat or other proteins or compounds can be used to regulate the activity of the inhibitor.

SPDP will react with terminal as well as epsilon amino groups, Since derivatization of a terminal amino group can inactivate a biologically active protein, T-BLOCK (Pierce Chemical Co., Rockford, Illinois) may be used to block that group during SPDP-derivatization. The T-BLOCK is then removed after derivatization to restore biological activity.

The invention will be further understood from the following, non-limiting examples.

EXAMPLES

1. Pretreatment and Activation of Dacron

Dacron graft material (Meadox Medical, Inc., Oakland, N.J.) is sectioned into 1.0 cm lengths. The lubricant on and in the woven surface is removed by washing once for 1 hr with carbon tetrachloride, and twice with 100% $CH_3OH$. The methanol is removed by multiple water washes, followed by one wash in phosphate buffered saline (PBS), pH 7.4.

The graft material is then subjected to alkaline hydrolysis to increase available COOH groups. The material is treated with 0.5N NaOH at 50° C. for 1 hr. and then washed with $H_2O$ repeatedly. The activated material is placed into 100.0 ml of 10 mM water-soluble carbodiimide (EDC) in deionized water, pH 4.6–5.0, for 1 hr at RT with constant stirring. The material is removed and washed in PBS to remove excess unbound EDC.

2. Base Coat Application

The base coat is applied to the lumen of the Dacron graft material. The derivatized Dacron material is incubated in a 5% HSA solution in PBS at 1 ml/cm$^2$ graft material for 24 hr at RT with constant stirring. The graft is removed and washed in PBS to remove non-specifically bound HSA. Approximately 20 μg protein/mg Dacron is covalently bound.

The HSA-bound Dacron material is then incubated in a 1.0 mM solution of SPDP in PBS, pH 7.4, to bind SPDP to the HSA (100 mM SPDP/cm$^2$ base coat). Incubation is terminated after 30–40 min at RT. The graft is washed in PBS to remove nonspecifically bound SPDP.

3. Activation of SPDP on Base Coat and Measurement of Binding Site Density

The SPDP-linked material is dried and weighed to obtain its absolute weight. It is then placed in a 50 mM solution of dithiotreitol (DTT) in acetate buffer, pH 4.5 for 5 min at RT. This reaction releases pyridine-2-thione (P-2-T) from the bound SPDP, and simultaneously forms free sulphydryl (SH) groups on the base coat. The released P-2-T is quantitated by adsorption spectrophotometry at 343 nm using its extinction coefficient ($E=8.08\times10^3$), and is directly proportional to the quantity of bound SPDP or binding sites. The number of binding sites are calculated and expressed as moles of sites/g of Dacron. The material is then washed 5 times in PBS and 4 times in $dH_2O$.

Alternatively, sulfhydryl (SH) groups are covalently introduced to serum albumin-coated grafts with the use of Traunt's reagent. This means of SH group introduction provides equal or greater quantities of SH groups bound to the base coat as that of SPDP. However, this method is limited in that quantitation of the number of SH groups ultimately bound is difficult.

4. Linkage of SPDP to Thrombomodulin

Lyophillized thrombomodulin (American Bio-product Co., Parsippany, N.J.) is resuspended in deionized $H_2O$ at 10 μg/ml (or 1 U/ml). SPDP (Pharmacia, Piscataway, N.J.) is dissolved in 100% EtOH to 10 mM. One part thrombomodulin is mixed with four parts SPDP (mole:mole), and incubated for 30 min at RT. SPDP-bound thrombomodulin is separated from free SPDP and reaction by-products by chromatography on a G-25 column, the derivatized thrombomodulin being eluted first.

The binding of SPDP to thrombomodulin can be quantitated by the addition of DTT which liberates pyridine-2-thione (P-2-T) from SPDP bound to thrombomodulin, and which can be measured spectrophotometrically at 343 nm. From this measurement, the moles of SPDP bound to thrombomodulin can be calculated. The amount of P-2-T released is directly proportional to the number of SPDP substitution reactions (covalent linkages) that have occurred between the base coat SH groups and SPDP-thrombomodulin. One mole of thrombomodulin appears to bind greater than 1.0 moles of SPDP in the present study. The mole:mole ratio of TM:SPDP derivatization is only an estimate, however, results suggest that TM biochemically interferes with the spectrophotometric means of P-2-T quantitation, an anomaly seemingly peculiar to TM derivatization with SPDP.

5. Linkage of Derivatized Thrombomodulin to Base Coat

The base coat (having free SH groups available due either to reduction with DTT or to treatment with Traunt's reagent) is washed with PBS (to remove the DTT or Traunt's reagent). SPDP-linked thrombomodulin is then added to the graft at approximately 4.0 μg/cm$^2$ Dacron. The solution is incubated overnight at RT to allow the binding of SPDP-thrombomodulin to SH groups on the Dacron graft. The Dacron material with thrombomodulin covalently immobilized thereto is then washed and stored in PBS.

6. Thrombomodulin Activity Assay

The following reagents were prepared (1) thrombomodulin (TM): 10 μg (1 U vial, American Bioproducts Co., Parsippany, N.J.) was reconstituted with 1 ml $dH_2O$; (2) Protein C (PC): 100 μg protein (10 PEU/vial, American Bioproducts Co.) was reconstituted with 1 ml $dH_2O$ (=0.1 μg/μl PC stock solution), and 10 μl of stock solution was diluted into 190 μl TM buffer (20 mM Tris-HCl, pH 8.0, 0.15M NaCl, 10 mM $CaCl_2$, 0.1% BSA) for use in the assay; (3) thrombin (T): a 25 U/ml solution was prepared from a 1:4 dilution of a 100 U/ml stock solution with TM buffer; (4) hirudin (H): 2 mg (Ciba-Geigy, Summit, N.J.) was reconstituted 1.913 ml TM buffer (11500 U/ml); (5) S-2266: a 4 mM solution was prepared by mixing 2.318 mg in 1 ml $dH_2O$; (6) assay buffer is 25 mM Tris-HCl, pH 8 0, 0.15M NaCl).

200 μl of the diluted PC solution, 5 μl of 25 U/ml T, and 50 μl of stock TM solution were mixed and incubated at 37° C. for 30 min. Five control samples not containing TM were also made and incubated at 37° C. for 30 min.

After the incubation, 10 μl of stock H solution and 740 μl of assay buffer was then added to inhibit excess thrombin. The samples are shown in TABLE 4.

TABLE 4

| sample no. | diluted PC | T | stock TM | TM buffer | H |
|---|---|---|---|---|---|
| 1* | 200 µl | 5 µl | — | 50 µl | 10 µl |
| 2* | 200 µl | 5 µl | — | 60 µl | — |
| 3* | — | 5 µl | — | 250 µl | 10 µl |
| 4* | — | 5 µl | — | 260 µl | — |
| 5* | 200 µl | — | — | 65 µl | — |
| 6** | 200 µl | 5 µl | 50 µl | — | 10 µl |

*control sample
**test sample

These solutions were incubated at 37° C. for 3 min. They were then transferred to cuvettes, and 50 µl of 4 mM S-2266 was added to each. The absorbance at $A_{405}$ was measured for 5 min., with readings taken every 13 sec. The ΔA/min. was also calculated.

The change in absorbance $A_{405}$/min. of the TM test sample (#6) was higher than in any of the control samples, indicative of TM activity. The ΔA/min. of the TM test sample was stable and consistent; 50 µl of TM stock solution (1 U/ml) gave a ΔA/min. of about 0.06, or 0.05 units of TM expresses a ΔA/min. of 0.06 at 405 nm using the chromogenic substate S-2266 under these conditions. The test mechanism is:

a. TM + T ⟶ TM-T complex.

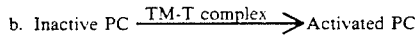
b. Inactive PC —TM-T complex→ Activated PC

c. S-2266 + Activated PC ⟶ increased $A_{405}$

7. Activity of SPDP-Derivatized Thrombomodulin

200 µl of stock TM solution was put into a cuvette. 10 µl of 11.0 µM SPDP (in TM buffer and EtOH) was added, and the $A_{343}$ before and after SPDP addition was measured. The solution was incubated at RT for about 30 min. The TM solution was allowed to stand for about 30 min. before 50 µl was assayed for activity using the same procedure described in EXAMPLE 1.

From the ΔA/min. values and as shown in FIG. 4, the TM-SPDP sample (#6) demonstrated activity (i.e., the ability to activate PC in the presence of thrombin).

8. Activity of Immobilized Derivatized TM (#1)

6 Dacron graft patches that were previously prepared as described in EXAMPLES 1 and 2, and stored in phosphate buffered saline (PBS)+Na azide, were washed 2 times in PBS and 1 time with PBS+sodium dodecyl sulfate (SDS). They were then sonicated and washed 3 times in PBS. The grafts were put into clean test tubes and incubated with 20 mM Traunt's reagent in PBS buffer for about 2 hr at RT.

A solution of TM-SPDP was made by mixing 500 µl of stock TM (1 U/ml) with 10 µl of 22.0 µM SPDP. The solution was incubated at RT for about 30 min. It was then purified on a G-25 column (Pharmacia, Piscataway, N.J.) to separate TM-SPDP from free SPDP.

Bovine serum albumin (BSA)-SPDP was prepared as a control in the evaluation of TM-bound Dacron grafts. A solution of BSA-SPDP was made by mixing 2 ml of 1% BSA with 62 µl of 20 mM SPDP. The solution was incubated at RT for 30 min. before being purified on a PD-10 column (Pharmacia, Piscataway, N.J.). The first peak of each sample was collected. The $A_{343}$ of a 1:5 dilution was measured before and 5 min. after the addition of 50 µl of 100 mM DTT to each ml of solution.

The grafts were washed 5 times in PBS after treatment with Traunt's reagent. 0.5 µl of TM-SPDP solution was added to grafts #1 and #2, and 0.5 µl of BSA-SPDP solution was added to grafts #3 and #4 (see TABLE 5). The grafts were allowed to incubate overnight at RT to immobilize TM on the test grafts and BSA on the control grafts.

TABLE 5

| graft # | graft type | treatment |
|---|---|---|
| 1 | immobilized TM | PC + T + H |
| 2 | immobilized TM | PC + T + H |
| 3 | immobilized BSA | PC + T + H |
| 4 | immobilized BSA | PC + T + H |

The grafts were then washed 2 times in PBS and 3 times in TM buffer. They were put into clean polyproplyene tubes and assayed for activity. 200 µl of PC (0.1 µg/µl) was added to each graft and mixed, followed by 5 µl of Thrombin (25 U/ml). They were incubated at 37° C. for 30 min. 10 µl of 11,500 U/ml H and 740 µl of assay buffer were added to each tube, which was then incubated for 3 min. at 37° C. Each sample was then put into a cuvette. 50 µl of 4 mM S-2266 was added, and the $A_{405}$ was measured for 5 min.

As shown in FIG. 5, the TM-immobilized grafts demonstrated greater activity in the assay when compared with the BSA-immobilized grafts as controls. The approximate ΔA/min. for the TM grafts was 0.004, and for BSA grafts, was 0.001. The ΔA/5 min. for the TM grafts was 0.013, and for the BSA grafts, was 0.005. The TM grafts demonstrated an increase in activity in the PC assay over the activity of the BSA grafts, which shows that TM has been immobilized to the graft and retains its activity.

9. Activity of Derivitized, Immobilized TM (#2)

400 µl TM was derivitized with 10 µl of 22 µM SPDP in EtOH. The solution was run through a G-25 column to purify and arrest the run after 30 min. The first peak fractions were collected and not pooled. 1.0 ml of 1% BSA in PBS was mixed with 31 µl of 22 µM SPDP in EtOH to form a control graft. After 30 min. the solution was run through a G-25 column. The first peak fractions were collected and pooled. 5 grafts were washed 5 times with PBS, and then sonicated in PBS+0.1% SDS to insure removal of noncovalently bound albumin. Each graft was incubated at RT for about 2 hr in 1 ml of 20 mM Traunt's reagent in PBST (PBS buffer+0.1% Tween 20). The grafts were washed 2 times in PBST and 3 times in PBS. As shown in TABLE 3, graft #1 was incubated with 0.5 ml of the first fraction of the TM-SPDP peak ($A_{280}$=0.142); graft #2 was incubated with about 0.4 ml of the TM-SPDP solution ($A_{280}$=0.036) of the second fraction; and grafts #3 and #4 were incubated with 0.5 ml of BSA-SPDP solution.

The $A_{343}$ of each solution was measured at t=0 using PBS as the blank. The grafts were then allowed to incubate overnight at RT. The $A_{343}$ of each solution was measured as an attempt to estimate the degree of TM immobilization. The grafts were washed 2 times in PBS and 3 times in TM buffer to remove noncovalently bound TM. The grafts were assayed for activity as described in EXAMPLE 8 except that PC (50 µl +950 µl TM buffer) was added before T (30 µl +210 µl TM buffer). The $A_{405}$ was measured over a 10 min. period.

TABLE 6

| graft # | graft type | treatment |
|---------|------------|-----------|
| 1 | immobilized TM | PC + T + H |
| 2 | immobilized TM | PC + T + H |
| 3 | immobilized BSA | PC + T + H |
| 4 | immobilized BSA + TM solution | TM + PC + T + H |

As shown in FIG. 6, the TM-immobilized grafts (#1 and #2) showed more activity than the BSA-immobilized graft (#3). Graft #4 with free TM in solution as a positive control did not show significant activity TM graft #1 was incubated in a solution with approximately three times the TM-SPDP than graft #2 Immobilized TM graft #1 demonstrated two times greater activity than did immobilized TM graft #2, indicating that there is a relationship of proportionally greater TM bound to that graft. TM grafts µl and #2 had 5 times and 2 times the ΔA (respectively) as BSA-blocked graft #3.

These results indicate that TM can be successfully immobilized to the surface of Dacron graft material, that immobilized TM retains thrombogenesis inhibiting activity, that added T can be bound by the immobilized TM, and that TM-bound T is capable of activating Protein C. Immobilized TM serves to enhance thromboresistance, as activated Protein C degrades Factor Va and VIIIa, thus inhibiting thrombus formation.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A biocompatible, thromboresistant substance comprising:
   (a) a synthetic, polymeric, biocompatible material;
   (b) at least one biocompatible base coat layer adhered to at least one surface of said material; and
   (c) a thrombogenesis inhibitor immobilized on said base coat layer via a component capable of binding said thrombogenesis inhibitor, said inhibitor being thrombomodulin or an active analog or active fragment thereof.

2. The substance of claim 1 wherein said polymer is selected from the group consisting of polyethylene terephthalate, nylon, polyurathane, cross-linked collagen, polyglycolic acid, polytetrafluoroethylene, and mixtures thereof.

3. The substance of claim 2 wherein said polymer comprises polyethylene terephthalate.

4. The substance of claim 1 wherein said base coat layer comprises a component selected from the group consisting of a protein, peptide, lipoprotein, glycoprotein, glycosaminoglycan, hydrogel, synthetic polymer, and mixtures thereof.

5. The substance of claim 4 wherein said component of said base coat layer comprises a protein.

6. The substance of claim 5 wherein said protein is selected from the group consisting of serum albumin, fibronectin, and mixtures thereof.

7. The substance of claim 6 wherein said protein comprises human serum albumin.

8. The substance of claim 6 wherein said protein comprises human fibronectin.

9. The substance of claim 1 further comprising a bifunctional cross-linking reagent linking said thrombogenesis inhibitor to said base coat layer.

10. The substance of claim 9 wherein said bifunctional cross-linking reagent comprises a heterobifunctional cross-linking reagent.

11. The substance of claim 9 wherein said bifunctional cross-linking reagent is homobifunctional.

12. A method of producing a biocompatible, thromboresistant substance, said method comprising the steps of:
   (a) adhering at least one base coat layer to at least one surface of a synthetic, polymeric, biocompatible material, said base coat layer including a component capable of binding a thrombogenesis inhibitor, said inhibitor being thrombomodulin or an active analog or active fragment thereof; and
   (b) immobilizing said thrombogenesis inhibitor to said base coat layer.

13. The method of claim 12 wherein said adhering step comprises adhering a base coat layer to at least one surface of said material, said base coat layer including a component selected from the group consisting of a protein, peptide, lipoprotein, glycoprotein, hydrogel, glycosaminoglycan, synthetic polymer, and mixtures thereof.

14. The method of claim 13 wherein said adhering step further comprises adhering a base coat layer containing a protein to at least one surface of said material.

15. The method of claim 14 wherein said adhering step further comprises adhering a base coat layer to at least one surface of said material, said base coat layer including a protein selected from the group consisting of serum albumin, fibronectin, and mixtures thereof.

16. The method of claim 12 wherein said adhering step comprises:
   (a) activating said synthetic material to enhance the binding of said base coat layer thereto; and
   (b) contacting said activated synthetic material with said base coat layer for a time sufficient to allow said base coat layer to bind to said activated synthetic material.

17. The method of claim 16 wherein said activating step comprises the steps of:
   (a) treating said synthetic material with a solution that makes available for binding at least one chemically reactive group in said material; and
   (b) contacting said treated synthetic material with a bifunctional cross-linking reagent for a time sufficient to allow binding of said chemically reactive group to said reagent.

18. The method of claim 17 wherein said treating step further comprises treating said synthetic material with a solution that makes available for binding at least one chemically active group in said material, said chemically active group being a carboxylic acid group.

19. The method of claim 12 wherein said immobilizing step comprises the steps of:
   (a) contacting said thrombogenesis inhibitor with a at least one molecule of a bifunctional cross-linking reagent for a time sufficient to allow said reagent to link to said thrombogenesis inhibitor; and
   (b) binding said reagent linked to said thrombogenesis inhibitor to said base coat layer.

20. The method of claim 19 wherein said contacting step further comprises contacting said base coat with at least one molecule of said bifunctional cross-linking reagent for a time sufficient to allow linking of said agent to said base coat layer, and
  said binding step further includes binding said thrombogenesis inhibitor-linked reagent to said base coat-linked reagent.

21. The method of claim 19 wherein said contacting step further includes contacting said thrombogenesis inhibitor with at least one molecule of said bifunctional cross-linking reagent selected from the group consisting of heterobifunctional cross-linking reagents, homobifunctional cross-linking reagents, and mixtures thereof.

22. The method of claim 20 wherein said contacting step further comprises the steps of:
  (a) reducing said base coat-linked reagent to expose a sulfhydryl group thereon;
  (b) adding said inhibitor-linked reagent to said reduced base coat-linked reagent; and
  said binding step comprises a substitution reaction involving said sulfhydryl group and said inhibitor-linked reagent, said reaction resulting in disulfide linkage of said inhibitor to said base coat layer.

23. A method of producing a biocompatible, thromboresistant substance, said method comprising the steps of:
  (a) linking a thrombogenesis inhibitor to a base coat material, said base coat material including a component capable of binding said thrombogenesis inhibitor, said thrombogenesis inhibitor being thrombomodulin or an active analog or active fragment thereof; and
  (b) immobilizing said thrombogenesis inhibitor-linked base coat material to at least one surface of a synthetic, polymeric, biocompatible material.

24. The method of claim 23 wherein said immobilizing step comprises:
  (a) activating said synthetic material to enhance the immobilization of said thrombogenesis inhibitor-linked base coat material thereto; and
  (b) contacting said activated synthetic material with said thrombogenesis inhibitor-linked base coat material for a time sufficient to allow said base coat material to become immobilized to said activated synthetic material.

25. The method of claim 23 wherein said thrombogenesis inhibitor-binding component of said base coat material is selected from the group consisting of a protein, peptide, lipoprotein, glycoprotein, hydrogel, glycosaminoglycan, synthetic polymer, and mixtures thereof.

26. The method of claim 25 wherein said thrombogenesis inhibitor-binding component of said base coat material comprises a protein.

27. The method of claim 26 wherein said thrombogenesis inhibitor-binding component of said base coat material comprises a protein selected from the group consisting of serum albumin, fibronectin, and mixtures thereof.

28. The method of claim 24 wherein said activating step comprises the steps of:
  (a) treating said synthetic material to make available for binding at least one chemically reactive group on said synthetic material; and
  (b) contacting said treated synthetic material with a bifunctional cross-linking reagent for a time sufficient to allow linking of said chemically reactive group to said cross-linking reagent.

29. The method of claim 23 wherein said linking step further comprises the steps of:
  a) contacting said thrombogenesis inhibitor with at least one molecule of a bifunctional cross-linking reagent for a time sufficient to allow linking of said reagent to said thrombogenesis inhibitor; and
  (b) adhering said thrombogenesis inhibitor-linked cross-linking reagent to said base coat material.

30. The method of claim 23 wherein said linking step further comprises the steps of:
  a) contacting said base coat material with at least one molecule of a bifunctional cross-linking reagent for a time sufficient to allow linking of said cross-linking reagent to said base coat material; and
  (b) adhering said base coat-linked cross-linking reagent to said thrombogenesis inhibitor.

31. The method of claim 30 wherein said contacting step further includes contacting said thrombogenesis inhibitor with at least one molecule of a bifunctional cross-linking reagent selected from the group consisting of heterobifunctional cross-linking reagents, homobifuntional cross-linking reagents, and mixtures thereof.

* * * * *